United States Patent [19]

Cebula

[11] Patent Number: 4,868,305
[45] Date of Patent: Sep. 19, 1989

[54] IMPROVEMENT IN THE PREPARATION OF INTERMEDIATES FOR QUINOLINE ANTIBACTERIAL AGENTS

[75] Inventor: Crispin R. Cebula, Albany, N.Y.

[73] Assignee: Sterling Drug Inc., New York, N.Y.

[21] Appl. No.: 155,948

[22] Filed: Feb. 16, 1988

[51] Int. Cl.$^4$ ............................................ C07D 215/56
[52] U.S. Cl. ...................................... 546/156; 560/43
[58] Field of Search ......................................... 546/156

[56] References Cited

U.S. PATENT DOCUMENTS 4,499,091  2/1985  Wentland et al. .................. 514/254

FOREIGN PATENT DOCUMENTS 627297  8/1949  United Kingdom ................ 546/156

OTHER PUBLICATIONS

Guo et al., Chemical Abstracts, vol. 106, No. 102233 (1987).
Koga et al., J. Med. Chem. 23, 1358–1363 (1980).

*Primary Examiner*—Mukund J. Shah
*Assistant Examiner*—E. Bernhardt
*Attorney, Agent, or Firm*—Thomas L. Johnson; Paul E. Dupont

[57] ABSTRACT

An improvement in the preparation and purification of lower-alkyl 7-choro-6-fluoro-1,4-dihydro-4-oxo-3-quinolinecarboxylate which involves preferential separation of its potassium salt from a dimethylformamide solution of the potassium salt of a mixture of said compound and its 5-chloro isomer.

4 Claims, No Drawings

IMPROVEMENT IN THE PREPARATION OF INTERMEDIATES FOR QUINOLINE ANTIBACTERIAL AGENTS

BACKGROUND OF THE INVENTION (a) Field of the Invention

This invention relates to an improvement in the process for preparing intermediates for the preparation of quinoline antibacterial agents.

(b) Information Disclosure Statement

Ethyl 7-chloro-6-fluoro-1,4-dihydro-4-oxo-3-quinolinecarboxylate is a known compound, described by Koga et al., J. Med. Chem. 23, 1358–1363 (1980). This reference describes the preparation of the compound according to the following flow-sheet:

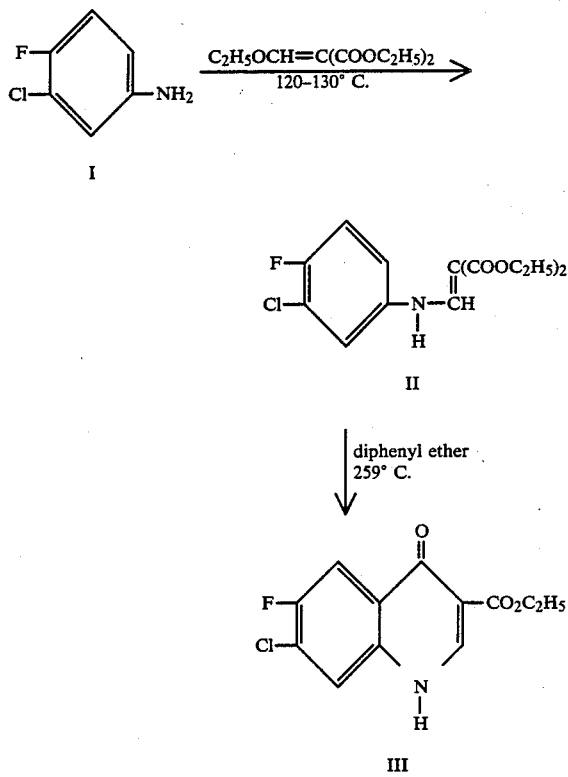

3-Chloro-4-fluoroaniline (I) and diethyl ethoxymethylenemalonate were heated at 120°–130° C. to give diethyl (3-chloro-4-fluorophenyl)aminomethylenepropanedioate (II). The latter was cyclized by heating it at reflux in diphenyl ether to give the quinoline III.

Koga et al. also describe the N-alkylation of III with potassium carbonate and ethyl iodide in dimethylformamide solution.

Wentland and Bailey U.S. Pat No. 4,499,091, issued Feb. 12, 1985 discloses Compound III as an intermediate for 1-amino-substituted-1,4-dihydro-4-oxo-6-fluoro-7-heterylquinoline-3-carboxylic acids, useful as antibacterial agents.

SUMMARY OF THE INVENTION

It has been discovered that the pyrolytic cyclization of Compound II produces, along with Compound III, substantial amounts (up to about 25%) of the isomeric ethyl 5-chloro-6-fluoro-1,4-dihydro-4-oxo-3-quinolinecarboxylate (IV):

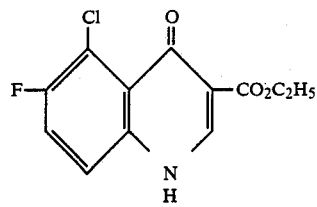

The presence of this undesired isomer, if carried through subsequent reactions in the synthesis of antibacterial agents, leads to difficulties in purification and lower yields.

It has now been found that the crude isomeric mixture of III and IV can readily be separated by crystallization of the potassium salt from a solution in dimethylformamide. The potassium salt of III separates from solution preferentially, substantially free of the 5-chloro isomer. The salt formation occurs at the nitrogen atom (1-position) of the quinoline nucleus.

Accordingly, in a process aspect, the invention relates to a process for the separation of an isomer mixture of lower-alkyl 7-chloro-6-fluoro-1,4-dihydro-4-oxo-3-quinolinecarboxylate and lower-alkyl 5-chloro-6-fluoro-1,4-dihydro-4-oxo-3-quinolinecarboxylate, which comprises cooling a solution of the potassium salt of said isomeric mixture in dimethylformamide to cause separation of the crystalline potassium salt of lower-alkyl 7-chloro-6-fluoro-1,4-dihydro-4-oxo-3-quinolinecarboxylate substantially free of the 5-chloro isomer.

The solution of the potassium salt is conveniently prepared by heating a suspension of said isomer mixture in dimethylformamide with an excess of potassium carbonate until conversion to the potassium salt is complete, and removing the excess potassium carbonate by filtration or an equivalent procedure.

In a composition of matter aspect, the invention relates to the potassium salt of ethyl 7-chloro-6-fluoro-1,4-dihydro-4-oxo-3-quinolinecarboxylate in crystalline form, substantially free of the potassium salt of the isomeric ethyl 5-chloro-6-fluoro-1,4-dihydro-4-oxo-3-quinolinecarboxylate.

DETAILED DESCRIPTION INCLUSIVE OF PREFERRED EMBODIMENTS

The term "lower-alkyl" as used herein refers to alkyl groups having from one to about four carbon atoms. A preferred alkyl group is ethyl.

In the formation of the potassium salt solution, a suspension of about 5–15% (w/w) of the isomer mixture in dimethylformamide is used. This is heated with potassium carbonate in at least about 50% molar excess and preferably about 100% molar excess. The suspension 10 is heated at a temperature between about 50°–100° C. until salt formation is complete, the time of which can vary from several minutes to several hours depending upon the temperature and the degree of excess of potassium carbonate. After removal of the excess potassium carbonate, 5 the resulting solution is cooled to about 0°–10° C. to cause crystallization of the potassium salt of Compound III. Further crops can be obtained upon concentration of the filtrates. These crops will contain substantial amounts of the potassium salt of IV but can be processed further by dissolving them in dimethylformamide and recrystallization therefrom to obtain additional quantities f pure potassium salt of III.

The following example will further illustrate the invention.

EXAMPLE

(a) Diethyl (3-chloro-4-fluorophenyl)aminomethylenepropanedioate (II).

3-Chloro-4-fluoroaniline (30.08 kg) in 8 L ethanol was heated at 40-50° C until a clear solution was obtained. Said solution was added to a 100 gallon glass-lined unit charged with 196 L ethanol. Diethyl ethoxymethylenemalonate (49.1 kg) was then added over an 80 minute period with stirring. The mixture was brought to reflux for one hour and then cooled to near 0° C. with stirring. Crystallization was initiated with seeding when the temperature had reached 27° C. during the cooling process. Stirring was continued for another hour, the solid product was filtered on a ceramic filter, and the filter cake was washed with 3×16 L cold (1°-5° C.) ethanol. The product was dried at 40° C. in vacuo for 19 hours to give 55.4 kg diethyl (3-chloro-4-fluorophenyl)aminomethylenepropanedioate, m.p. 71.5°-72.5° C. (85% yield). The combined filtrate and washes were concentrated to 54 L and a second crop was isolated and dried as before to give 5.6 kg additional product, m.p. 71.5°-72.5° C. for a combined yield of 93.5%.

(b) Ethyl 7-chloro-6-fluoro-1,4-dihydro-4-oxo-3-quinolinecarboxylate (III).

In a 30 gallon stainless steel unit, 55 L of Dowtherm A (a eutectic mixture of diphenyl and diphenyl ether) was stirred and heated at reflux (253°-257° C.) for one hour. To this was added a solution of 31.3 kg diethyl (3-chloro-4-fluorophenyl)aminomethylenepropanedioate in 10 L Dowtherm A held at 94°-98° C. The addition was effected over a period of four hours so that reflux of the reaction mixture was maintained. The reaction mixture was then allowed to cool and crystallization of the product began. After the temperature had reached 28°-30° C., the solid product was collected on a ceramic filter and washed with 2×9 L dimethylformamide (DMF). The damp filter cake was added to 65 L DMF in a 30 gallon kettle. The resulting slurry was heated at 90°-95° C. for 30 minutes and then cooled to 40° C. The solid was collected on a ceramic filter, washed with 2×8 L DMF and dried at 60° C. for 24 hours to give 23.8 kg ethyl 7-chloro-6-fluoro-1,4-dihydro-4-oxo-3-quinolinecarboxylate containing about 10% of the 5-chloro-6-fluoro isomer as indicated by NMR spectra.

The isomer mixture (28.5 kg comprising 14 kg of the above described product and 14.5 kg of an earlier run containing 25-30% of the 5-chloro isomer) was suspended in 285 L DMF in a 100 gallon glass-lined unit. To the stirred suspension was added 29.2 kg potassium carbonate. The mixture was heated to 75° C. for one hour, then cooled to 40° C. and filtered on a ceramic filter through a ½ inch filter aid pad to remove excess potassium carbonate. The filter cake was washed with 4×8 L warm (45°-50° C.) DMF. The combined filtrate and washes were returned to a 100 gallon glass-lined unit and cooled with stirring. At 32° C. crystallization ensued. Cooling was continued to 5° C. and the system was held at 5°-8° C. for 90 minutes. The solids were collected on a ceramic filter and the cake was washed with 4×8 L DMF (2°-5° C.) followed by a 2×6 L hexane (ambient temperature). The hexane washes were discarded. The filter cake was dried at 68° C. in vacuo for 24 hours to give 22.9 kg potassium salt of ethyl 7-chloro-6-fluoro-1,4-dihydro-4-oxo-2-quinolinecarboxylate containing Δ mole DMF of crystallization, substantially free of the 5-chloro isomer. Second and third crops (3.84 kg and 4.20 kg, resp.) were obtained by concentrating and cooling the corresponding filtrates and washes.

The crops of potassium salt were analyzed as follows:

|  | Crop I | Crop II | Crop III |
| --- | --- | --- | --- |
| Weight (kg) | 22.9 | 3.84 | 4.20 |
| Yield (based on K salt with ½ mole DMF) | 66% | 11% | 12% |
| 5-Chloro isomer content (based on NMR data) | trace | 15% | 50% |

A sample of the Crop I material was heated at 90° C. in vacuo for several days to remove the DMF of crystallization to give a solvent-free sample of the potassium salt of ethyl 7-chloro-6-fluoro-1,4-dihydro-4-oxo-3-quinolinecarboxylate as a colorless solid, m.p. above 300° C.

Anal. Calcd. for $C_{12}H_8ClFKNO_3$: C, 46.84; H, 2.62; N, 4.55; Found: C, 46.71; H, 3.03; N, 4.68.

A further sample (100 g) of the Crop I material was acidified with aqueous acetic acid (50 ml in 1 L water), heated at 80° C. for one hour. The product was filtered, washed with water and ethanol, and dried at 60° C. in vacuo to give 85 g ethyl 7-chloro-6-fluoro-1,4-dihydro-4-oxo-3-quinolinecarboxylate, colorless solid, m.p. above 300° C.

Anal. Calcd. for $C_{12}H_9ClFNO_3$: C, 53.75; H, 3.36; N, 5.17; Found: C, 53.44; H, 3.06; N, 5.08.

Alternatively, the ethanol solvent used in part (a) of the Example was replaced by Dowtherm A, and the resulting solution of compound II was directly cyclized according to part (b) without isolation of II.

It is further contemplated that if the diethyl ethoxymethylenemalonate in part (a) of the foregoing example is replaced by a molar equivalent amount of dimethyl ethoxymethylenemalonate and the subsequent procedure carried out as described, there can be obtained methyl 7-chloro-6-fluoro-1,4-dihydro-4-oxo-3-quinolinecarboxylate and its potassium salt in substantially pure form.

I claim:

1. In a process for the separation of an isomer mixture of lower-alkyl 7-chloro-6-fluoro-1,4-dihydro-4-oxo-3-quinolinecarboxylate and lower-alkyl 5-chloro-6-fluoro-1,4-dihydro-4-oxo-3-quinolinecarboxylate, said 5-chloro isomer being present in amounts up to about 25% of said mixture, the step which comprises cooling a solution of the potassium salt of said isomer mixture to about 0°-10° C. in dimethylformamide to cause separation of the crystalline potassium salt of lower-alkyl 7-chloro-6-fluoro-1,4-dihydro-4-oxo-3-quinolinecarboxylate substantially free of the 5-chloro isomer.

2. The process according to claim 1 in which lower-alkyl is ethyl.

3. The process according to claim 1 wherein said potassium salt solution is prepared by heating a suspension of said isomer mixture in dimethylformamide with a molar excess of potassium carbonate until conversion to the potassium salt is complete, and filtering the suspension to remove excess potassium carbonate.

4. The potassium salt of ethyl 7-chloro-6-fluoro-1,4-dihydro-4-oxo-3-quinolinecarboxylate in crystalline form, substantially free of the potassium salt of the isomeric ethyl 5-chloro-6-fluoro-1,4-dihydro-4-oxo-3-quinolinecarboxylate.

* * * * *